United States Patent [19]

Snyder et al.

[11] Patent Number: 5,089,395
[45] Date of Patent: Feb. 18, 1992

[54] VIABLE MICROORGANISM DETECTION BY INDUCED FLUORESCENCE

[75] Inventors: A. Peter Snyder, Bel Air, Md.; David B. Greenberg; Pasquale V. Scarpino, both of Cincinnati, Ohio

[73] Assignee: University of Cincinnati, Cincinnati, Ohio

[21] Appl. No.: 222,258

[22] Filed: Jul. 21, 1988

Related U.S. Application Data

[63] Continuation-in-part of Ser. No. 917,258, Oct. 8, 1986, abandoned, which is a continuation of Ser. No. 706,160, Feb. 27, 1985, abandoned.

[51] Int. Cl.$^5$ ............................................. C12Q 1/06
[52] U.S. Cl. .................................... 435/39; 435/14; 435/18; 435/19; 435/21; 435/29; 435/34
[58] Field of Search .................. 435/4, 18, 19, 21, 29, 435/34, 39, 291

[56] References Cited

U.S. PATENT DOCUMENTS 4,283,490  8/1981  Plakas .................................. 435/291

FOREIGN PATENT DOCUMENTS 54001    6/1982  European Pat. Off. .............. 435/34
122148   4/1983  European Pat. Off. .
2504679 10/1982  France .

OTHER PUBLICATIONS

Snyder et al., Biotechnology and Bioengineering, 26: 1395-1397, "Viable Microorganism Detection by Induced Fluorescence", Nov. 1984.
Godsey et al. (1981) Journal of Chemical Microbiology vol. 13, No. 3, pp. 483-490.
Bailey et al., Diagnostic Microbiology, pp. 72-73, 1966.
The Fisher Scientific Catalog, 1983 Edition pp. 286-287 and 326.

*Primary Examiner*—Sam Rosen
*Attorney, Agent, or Firm*—Frost & Jacobs

[57] ABSTRACT

The present invention concerns a spectrometric technique to determine microorganism detection and identification by taking advantage of the inherent extracellular enzymes present in living organisms, as opposed to dead, non-enzyme producing organisms. These enzymes are harnessed in the in vivo reactions with a non-fluorescent dye containing a select organic functional group that is known to be cleaved or hydrolyzed by the certain enzyme. The dye is tailored such that one of the products fluoresces, so that by employing a conventional spectrofluorimeter, the rate of fluorescence can be determined. By subjecting a plurality of samples having different cellular concentrations of viable microorganisms to the same non-fluorescent dye, or by subjecting the same bacterial sample to a number of different non-fluorescent dyes, a pattern of fluorescent rates emerge. By employing the pattern recognition set to standard microorganism fluorescent response curves, microorganism detection and identification can be determined. Thus, the present invention concerns a process for determining microorganism detection, identification and concentration.

6 Claims, 10 Drawing Sheets

VIABLE MICROORGANISM DETECTION BY INDUCED FLUORESCENCE

LICENSE RIGHTS

The U.S. Government has rights in this invention pursuant to Contract No. DAAK 11-83-K-0004 awarded by the U.S. Army Armament Research and Development Command. The invention described herein may be manufactured, used and licensed by or for the Government for governmental purposes without the payment of any royalty thereon.

CROSS-REFERENCE TO RELATED APPLICATIONS

This application is a continuation-in-part of application Ser. No. 06/917,258 filed Oct. 8, 1986, now abandoned, which is a continuation of application Ser. No. 06/706,160 filed Feb. 27, 1985, now abandoned.

BACKGROUND OF THE INVENTION

1. Field of the Invention

The present invention concerns the rapid detection and characterization of viable microorganisms based upon the technique of induced fluorescence. In particular, the present invention concerns employing a non-fluorescent dye substrate for microorganisms to metabolize extracellularly through an enzyme-specific reaction. A specific radiation source can be used to induce product fluorescence and the latter is detected by a conventional photomultiplier tube. Standard curves can be obtained by relating the effect of the microorganism activity to the initial rate of fluorescence generation in order to obtain the identification and estimation of the microorganism concentration.

2. Prior Art

A methodology for rapid detection and identification of microorganisms has long been a concern to the medical, pharmaceutical and food processing fields, among others. Because of this sustained interest, significant advances over the classical time consuming methods of plate counting, membrane filtration, or multiple tube fermentation procedures have been noted. However, these techniques require as much as one to three days in order to detect and identify microorganisms.

Various recent developments have been focused upon techniques in immunofluorescence, enzyme amplification, excitation-emission matrices with a video fluorometer of whole-cell supernatants and differential dye-cell wall binding, mass spectrometry, bacteriophage lysis, computer assisted probability methods, gel ferrography, and the double fluorescent DNA staining method coupled with flow cytometry. Each of these techniques is limited by disadvantages such as laborious and time-consuming laboratory preparation and sample handling, long observation times and nonspecificity with respect to microorganism characterization and subsequent identification. The following patents exemplify some of these prior art procedures.

U.S. Pat. No. 4,283,490 to Plakas discloses a method for detecting the concentration of certain reactive molecules from microbial cells in samples of fluids and degraded solids. A sample containing microbial cells is treated to eliminate substantially all non-microbial materials. The microbial cells are then caused to rupture and form a thin film positioned in the vicinity of a photodetector. An appropriate reagent contacts the thin film and the resulting photon emission is observed by the photodetector through an optical filter which selectively restricts the wave length of photons permitted to pass to the detector. The strength of the luminescence indicates the concentration of microbial cells in the sample.

French Patent 2,504,679 to Koumura, et al discloses a method of detecting microorganisms in a sample solution using a fluorescent analysis method with an umbelliferone derivative. The method consists of: (a) incubating an aqueous solution containing the sample solution and a non-fluorescent umbelliferone derivative at a temperature between 20° and 50° C. until the umbelliferone product is generated in the solution by microorganisms contained in the sample solution; (b) measuring the amount of umbelliferone product generated through induced fluorescence; and (c) determining the concentration of microorganisms in the sample solution from the amount of umbelliferone product generated. In this procedure, the non-fluorescent umbelliferone derivative is hydrolyzed and the umbelliferone product is generated by the microorganisms contained in the sample solution. The product can then be detected by induced fluorescence. The amount of umbelliferone product is approximately proportional to the number of microorganisms. According to the procedure, the microbial inspection is accomplished in one to twelve hours. Generally, it appears that the procedure is most often accomplished in six to twelve hours as evidenced by the examples set forth therein. Moreover, the length of incubation, which is the first step of the procedure, ranges from one to twelve hours itself. Accordingly, although the French patent may describe a procedure which is quicker than known prior art procedures, six to twelve hours for detecting microorganisms remains an unacceptable length of time and thus there remains a need for a quicker procedure.

SUMMARY OF THE INVENTION

The present invention is predicated on the principle that an enzymatic process in which a non-fluorescent dye compound is converted extracellularly to a fluorescent analog can be achieved only by a viable organism. The present invention of inducing microorganism metabolite fluorescence results in microorganism detection and concentration information in twenty to sixty minutes. Other characteristics of the present invention are: ester compounds in some of the non-fluorescent dyes are metabolized in most common types of water-borne microoganisms, which makes them a general purpose reagent for microorganism testing; and the assay technique, a non-destructive procedure for identifying viable microorganisms, is unaffected by the presence of dead microorganisms.

The present invention utilizes the following equation:
non-fluorescent enzyme→fluorescent dye
substrate+(in micro-product+metabolites
organisms)

This equation presents various modes of biochemical strategy in order to uniquely characterize a given non-fluorescent dye substrate and microorganism. The present invention pinpoints the identity of a particular enzyme that is indigenous to the microorganisms themselves. For the same microorganism enzyme a series of chemically similar compounds (e.g. esters) can be utilized to generate reaction rates and thus, associated product fluorescence.

According to the invention, there is provided a process for the detection, identification, and quantification of viable microorganisms of a minimum concentration not less than $10^3$ cells/ml within a time period of sixty minutes, comprising the steps of:

obtaining a plurality of samples suspected of containing viable microorganisms, preparing therefrom an array of separate samples each having different cellular concentrations by a magnitude of at least about 10;

adding the same non-fluorescent dye to a plurality of the array of separate samples, the dye being capable of being catalyzed by the suspected viable microorganisms;

reacting the dye with an enzyme produced by the viable microorganisms to yield a product which can be induced to fluoresce;

inducing fluorescence; and detecting the rate of product fluorescence of the reaction of each of the array of separate samples at different concentrations and identifying and quantifying the microorganisms based upon the particular dye employed and the rate of fluorescence of the produced product by comparison with a standardized series of curves constituting a pattern recognition set of fluorescent response rates.

Alternatively, instead of adding the same non-fluorescent dye to a plurality of the array of separate samples of different concentrations, the process includes adding different non-fluorescent dyes to each of the samples having the original concentration of viable microorganisms, the dyes being capable of being catalyzed by the suspected viable microorganism, and thereafter practicing the subsequent steps set forth above.

DESCRIPTION OF THE PREFERRED EMBODIMENTS

The method of the present invention is founded upon the principle that an enzymatic process in which a non-fluorescent dye is converted extracellularly to a fluorescent product can be achieved only by a viable organism. The various effective dyes were based on the common existence of certain enzyme systems found in most living bacteria.

Either a laser source or fluorimeter can be used in the detection phase of enzyme-containing microorganisms. The rate of reaction proceeds at the organism's inherent rate.

The success of the method of the present invention depends upon four criteria: (1) the non-fluorescent dyes that are used must be readily metabolized by the microorganism; (2) the dyes must be capable of being converted to a fluorescent product based upon an enzymatic reaction; (3) the reaction must be endogenous in nature for the results to reflect the presence of viable microorganisms; and (4) in order to detect very low microorganism concentrations, the dye must have a relatively high quantum yield.

The mechanism of the dye metabolism is essentially a one step process. It consists of the extracellular enzymatic hydrolysis of the non-fluorescent dye. Furthermore, it has been hypothesized that although many types of microorganisms metabolize the same dye, each will have its own characteristic kinetics. Suitable dyes for the present invention should be nonpolar and enzymatically capable of reacting with most microorganisms to provide a stable product of known fluorescence. Exemplary of non-fluorescent dyes which produce fluorescent products when reacted with enzymes from live microorganisms are: indoxyl acetate, 4-methylumbelliferone galactoside, 4-methylumbelliferone phosphate, indoxyl glucoside, diacetylfluorescein, beta-naphthyl acetate, 4-methylumbelliferone glucoside, homovanillic acid, butyrylresorufin, thiamine (vitamin $B_1$), or the like. Note that any dye capable of producing a fluorescent product upon reaction with microorganisms would be acceptable for conducting the method of the present invention.

In order to carry out the method of the present invention, it is essential that one skilled in the art be knowledgable of the enzymes produced by the microorganism to be detected. In this manner, one skilled in the art can select a proper dye which will act with the enzyme so as to produce a fluorescent product, such as those disclosed in Table 1.

The more ubiquitous microorganisms whose detection is desired and are found in water, sewage, food and pharmaceuticals are *Bacillus globigii* (subtilis), *Bacillus pumilis, Saccharomyces cerevisiae, Pseudomonas stutzeri, Proteus vulgaris, Serratia marcescens*, and *Escharichia coli.*

The organisms *Bacillus subtilis* variant niger (*Bacillus globigii*) (BG), *Bacillus pumilis* (BP), *Saccharomyces cerevisiae* (SC), *Pseudomonas stutzeri* (PS), *Proteus vulgaris* (PV), *Serratia marcescens* (SM) and *Escherichia coli* (EC) were grown on tryptose plate-cultures for 48 hours. The heavy organism growth was transferred to sterile test tubes by using 2 ml of a pH 7.5, 0.1M $KH_2PO_4$ sterile buffer. Centrifugation at 3500 rpm for 0.5 hours and subsequent resuspension of the pellet in phosphate buffer were performed to remove residual tryptose growth medium. The suspensions were stored at 4° C.

Assay conditions for each non-fluorescent dye are:

(a) Indoxyl acetate. To 1.8 ml of sterile phosphate buffer, 0.1 ml of a 1:100 acetone dilution of a solution of 10 mg indoxyl acetate/ml acetone and 0.1 ml of the bacterial sample are added together.

(b) Indoxyl-$\beta$-D-glucoside. To 1.8 ml of sterile 0.1M tris, pH 7.5 (tris buffer), 0.1 ml of a 1:100 aqueous solution of a 6.31 mg indoxyl-glucoside/ml tris buffer and 0.1 ml of bacterial suspension are added together.

(c) 4MU-$\beta$-D-glucoside. To 1.8 ml of sterile tris buffer, 0.1 ml of a 3.38 mg 4MU-glucoside/ml tris buffer and 0.1 ml of bacterial sample are added together.

(d) 4MU-phosphate. To 1.8 ml of sterile tris buffer, 0.1 ml of a 1:10 aqueous solution of 12.67 mg 4MU-phosphate/ml tris buffer and 0.1 ml of bacterial suspension are added together.

(e) 4MU-$\beta$-D-galactoside. 2.0 mg of 4MU-galactoside are dissolved in 40 ml of phosphate buffer and 0.1 ml of a bacterial sample is added to 1.9 ml of the 4MU-glactoside/phosphate buffer solution.

(f) 3-indoxyl phosphate. To 1.8 ml of sterile tris buffer, 0.1 ml of a 1:10 aqueous solution of a 2.57 mg indoxyl phosphate/ml tris buffer and 0.1 ml of a bacterial suspension are added together.

(g) Diacetylfluorescein (DAF). The bacterial assay solution was prepared as follows: 2 mg of diacetylfluorescein was dissolved in 5.0 ml of acetone, and 2.5 ml of this solution was diluted with 50 ml of phosphate buffer in a volumetric flask to be used within 2 hours of preparation. For the dissolution of DAF, methylcellosolve and acetone are solvents of choice. Acetone afforded an increase in the rate of DAF hydrolysis by a factor of 2.6. Hence, acetone was preferred as the substrate solvent. Two milliliters of the DAF solution was transferred to a cuvette, 0.1 ml of bacterial suspension was added and, with a piece of parafilm, the cuvette was briefly shaken. A fluorimeter was used to determine the fluorescence of each sample. The excitation and emission slits were 1 nm and 5 nm, respectively. The temperature of each assay sample was controlled to 26+1° C. Bacterial concentration was determined by the viable plate count method. Pour plates of tryptose agar with aliquots of bacteria were prepared in triplicate per each assay sample. The rate of fluorescence generation was performed by determining the slope of a tangent to the initial portion of the fluorescent generation curve. Each fluorescent experimental data point represents an average of 2-5 assays. The fluorimeter was calibrated with a borosilicate glass standard (ex=310 nm, em=350 nm).

The rate of fluorescence generation was monitored by varying the bacterial concentration by a magnitude of at least about 10 while keeping the concentration of the same dye constant and then plotting the rates on a Log scale (FIGS. 1-9).

Figure 1A:
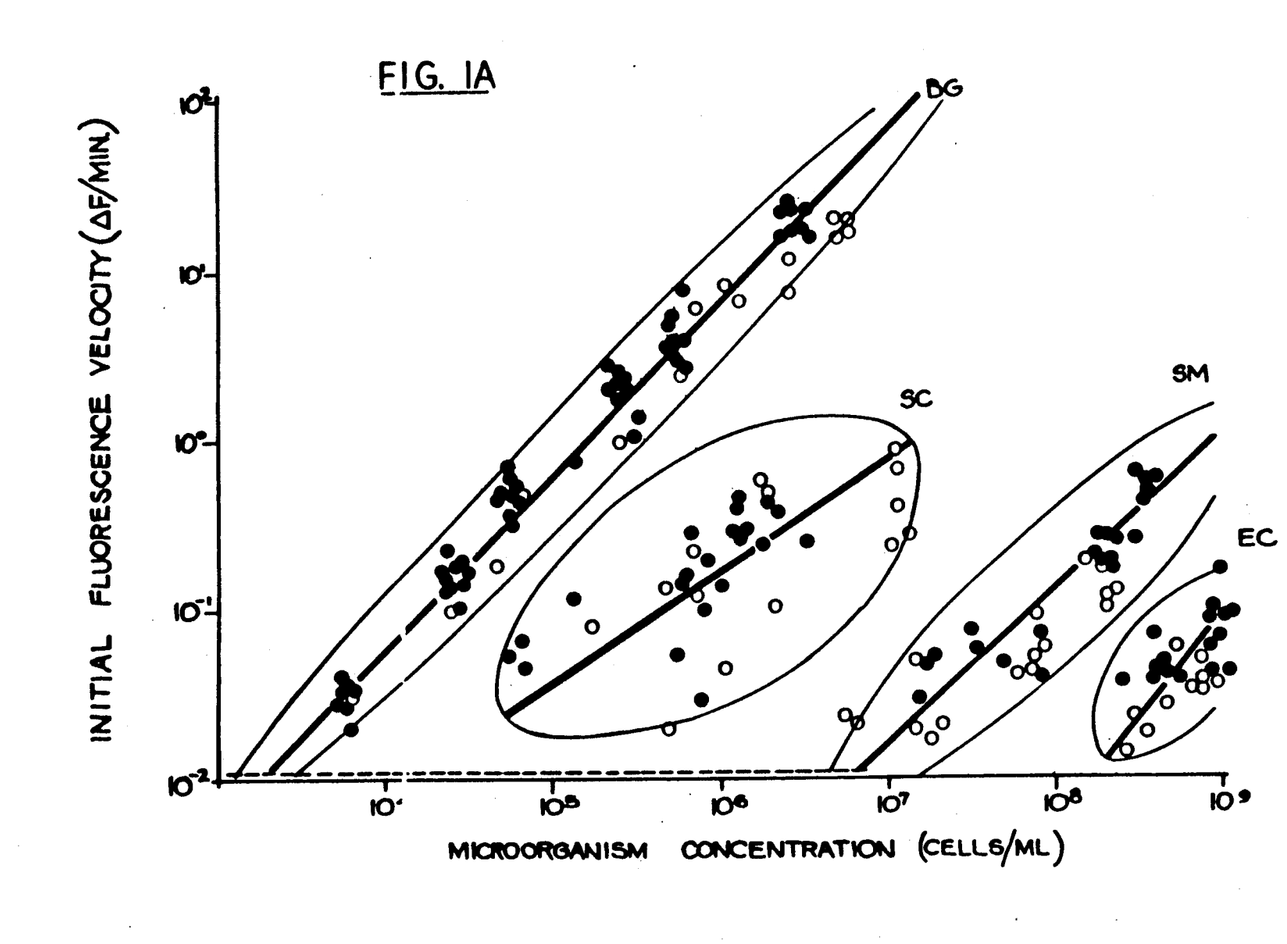
FIG. 1a illustrates a graph of the initial velocity of fluorescein from the non-fluorescent dye diacetylfluorescein as a function of microorganism concentration. Each symbol represents a separate microbial suspension. The horizontal, dotted line at 0.011 $\Delta F$/min. represents the non-fluorescent dye spontaneous hydrolysis fluorescence rate. Each symbol for individual organism species represents a separate suspension except for the BG which represent two microbial suspensions. For BG, the solid circle and open circle symbols represent data taken over a period of one month and three days, respectively, while the same symbols for the organisms EC, SM and SC represent data taken at two weeks and one week, respectively.
Figure 1B:
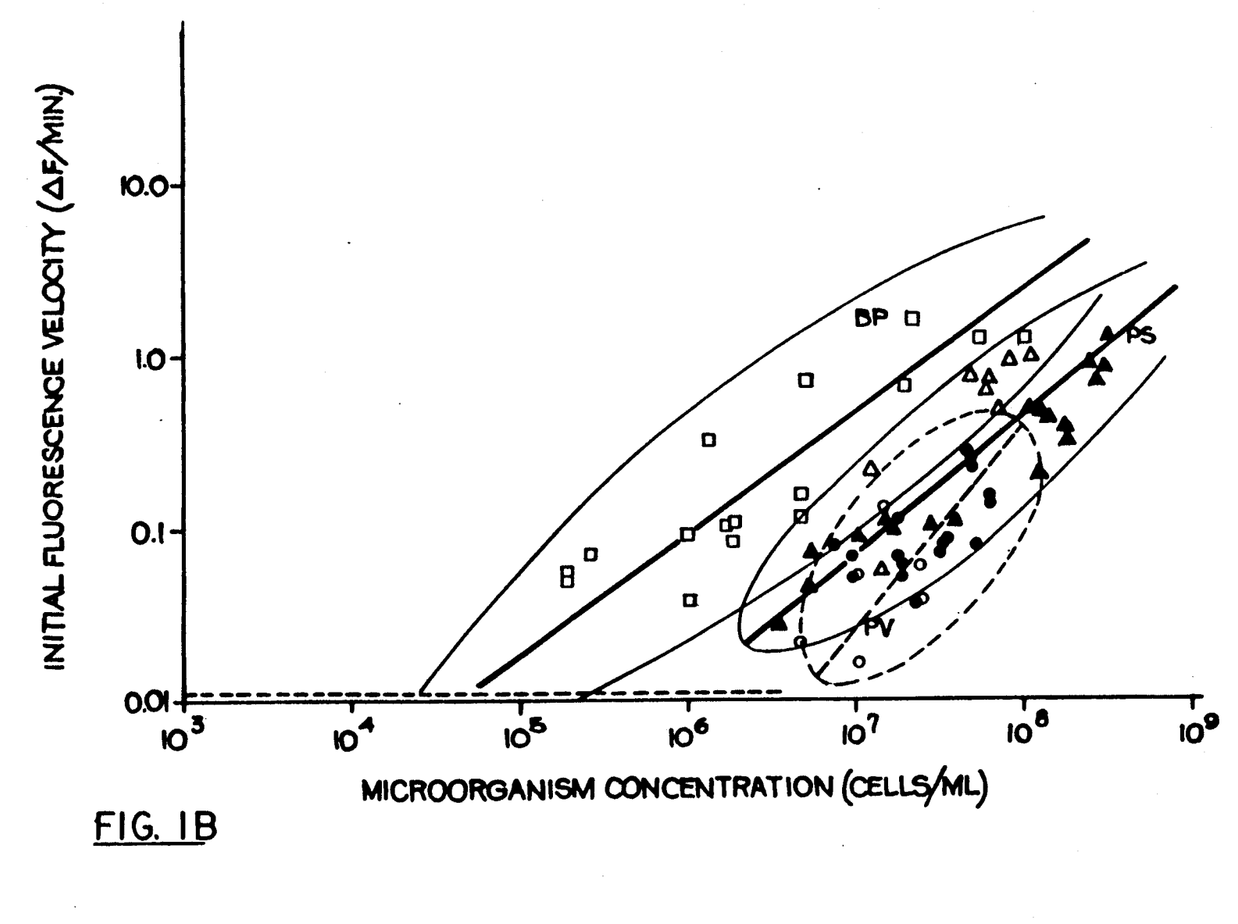
FIG. 1b presents a graph of the initial velocity of fluorescein from diacetylfluorescein as a function of microorganism concentration like that illustrated in FIG. 1a, except the graph illustrates the microorganisms PV, BP and PS. The BP data was taken over a two-week interval, while for PS and PV, the data represents two and one week intervals for the shaded and unshaded symbols, respectively, BP ($\square$), PS ($\Delta$, $\blacktriangle$), PV (O, ●).

On the concentration/velocity plot (FIGS. 1-9) the response of each organism occupies a certain region which reflects its particular enzyme-production capacity. In the absence of organic nutrients, repeated plate counts of all suspensions showed that each organism existed only in a vegetative state with minimal changes in viable concentration occurring over time. Typical examples in FIG. 1 are shown on the following sets of data: solid symbols occurring at $2.0-3.0 \times 10^5$ cells/ml (BG), $1.40-2.20 \times 10^6$ cells/ml (SC), $2.0-3.0 \times 10^8$ cells/ml (SM); and open symbols at $1.0-1.5 \times 10^7$ cells/ml (SC). Each symbol for each individual organism specie represents a separate suspension except for the BG open symbols, which represent two microbial suspensions. For BG, both solid and open symbols represent data taken over a period of one month and three days, respectively, while for the three other organisms, they correspond to two and one week time periods, respectively. Different suspensions of the same microorganisms yield a similar response, which over the observed time periods, show that a general decrease in the initial rate of fluorescein fluorescence took place for the microorganisms BG and SC. A less defined temporal response was noted for SM and SC. There are a number of possible factors that can contribute to these latter observations. The cellular aging might lead to such effects as cell modification, alterations in its capacity to produce lipase/lipolytic enzymes, enzyme conformations different from that of the same enzyme produced in a relatively young cell, or any combination of these possibilities.

Additionally, it can be inferred from FIG. 1 that the fluorescent response of relatively high concentrations ($10^6-10^7$ cells/ml) of some common microorganisms such as EC and SM in a competing medium, have essentially no effect on the DAF fluorescent response produced by low concentrations of other microorganisms, e.g., BG and SC. This is because the former generate such a low level fluorescent output that they do not spectrally interfere with the lipase/DAF reaction of the latter organisms. It can also be observed from FIG. 1 that even for these latter two organisms, the ubiquitous SC contributes no better than 14% of an enzymatic fluorescent effect to the lipase reaction of BG at a concentration of $10^4$ cells/ml and only 6% at $10^5$ cells/ml. A similar comparison can be made of the EC:SM pair in that no more than 6% contribution of EC would occur at similar concentrations. PS and PV (FIG. 1b) display similar responses yet both contribute approximately 10% and essentially no lipolytic reaction interference in the presence of SC and BG, respectively, at similar concentrations. It can be shown that PS and PV would effect approximately 11% fluorescence interference with BP. However, the latter displays kinetics similar to SC but only produces about a 2% interference with the other Bacillus organism tested, BG, over the same range of concentrations.

The limit of microorganism sensitivity is considered to be the particular concentration of an organism that produces twice the initial velocity of product fluorescence to that rate of fluorescence attributed to the spontaneous hydrolysis of the non-fluorescent dye. These values were determined from the point where the major axis of the 95% ellipse intersects twice the spontaneous hydrolysis velocity of fluorescence.

A summary of the detection limits of the microorganism-non-fluorescent dye pairs that produce a fluorescent response is presented in Table 2. Note the detection limits for the organisms with the ester-non-fluorescent dyes (DAF and indoxyl acetate). The bacilli for these non-fluorescent dyes show a 10-fold increase in sensitivity in comparison of their indoxyl acetate to diacetylfluorescein activity. Other microorganisms show similar sensitivities, however, it appears that indoxyl acetate is a more sensitive probe of lipolytic activity than is diacetylfluorescein. With the glucoside non-fluorescent dyes, both bacilli display greater sensitivity to the 4MU derivatives versus the indoxyl derivatives. However, a different phenomenon is obtained with SM and EC using the phosphate substrates. SM displays 4 times greater sensitivity to indoxyl phosphate than with 4MU-phosphate, while EC is observed to be 3 times less sensitive in the same non-fluorescent dye comparison. These differences aid in bacterial identification using the pattern recognition set.

ANALYSIS OF RESULTS

FIGS. 1-9 constitute the pattern recognition set obtained with the different microorganisms and the different non-fluorescent dyes. The results are set forth for the in vivo extracellular enzyme response patterns with their respective non-fluorescent dyes.

Diacetylfluorescein. It can be inferred from FIG. 1a that the fluorescent response of relatively high concentrations ($10^6-10^7$ cells/ml) of some common organisms, such as EC and SM, have essentially no effect on the diacetylfluorescein fluorescent response produced by low concentrations of other microorganisms, BG and SC. This is because the former generate such a low level fluorescent output that they do not spectrally interfere with the lipase-diacetylfluorescein reaction of the latter organisms. It can also be observed from FIG. 1a that SC contributes no better than 14% of the enzymatic fluorescent effect to the lipase reaction of BG at a concentration of $10^4$ cells/ml and only 6% at $10^5$ cell/ml. A similar comparison can be made of the EC:SM pair in that no more than an 6% contribution of EC would occur at similar concentrations.

Figure 2:
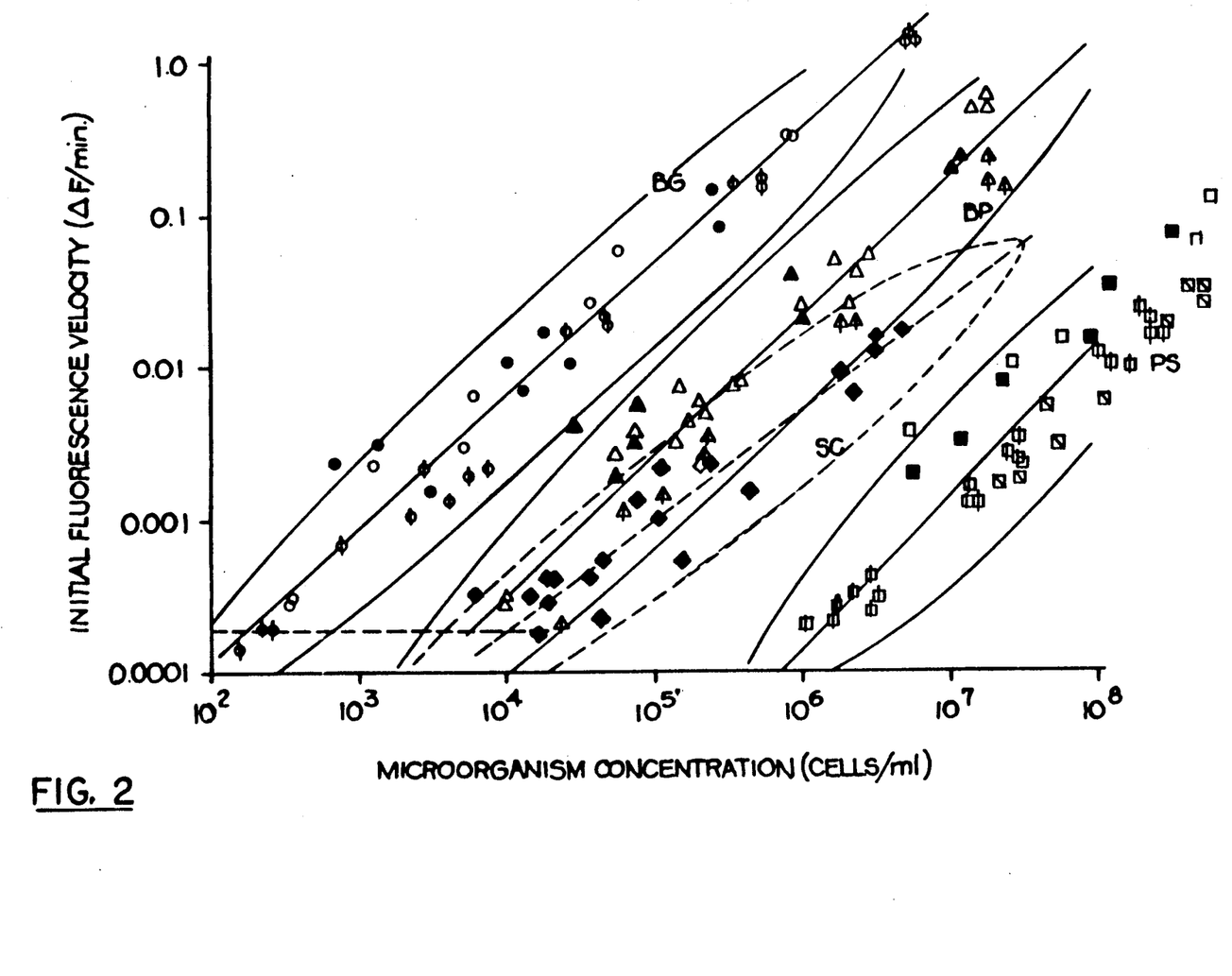
FIG. 2 is a graph of the initial velocity of indoxyl fluorescent from the substrate indoxyl acetate as a function of microorganism concentration. The microorganisms shown are BG, BP, SC, and PS. The horizontal-line at 0.00018 F/min. represents the substrate spontaneous hydrolysis fluorescence rate. Three separate samples for the microorganisms BG and BP are illustrated in the graph wherein BG is represented by an (O, ●, $\Phi$) and BP ($\Delta$, $\blacktriangle$, $\triangle$) while the microorganism SC is represented by (♦) and the microorganism PS is represented by four different samples as ($\square$, ■, $\square$, $\square$).
Figure 3:
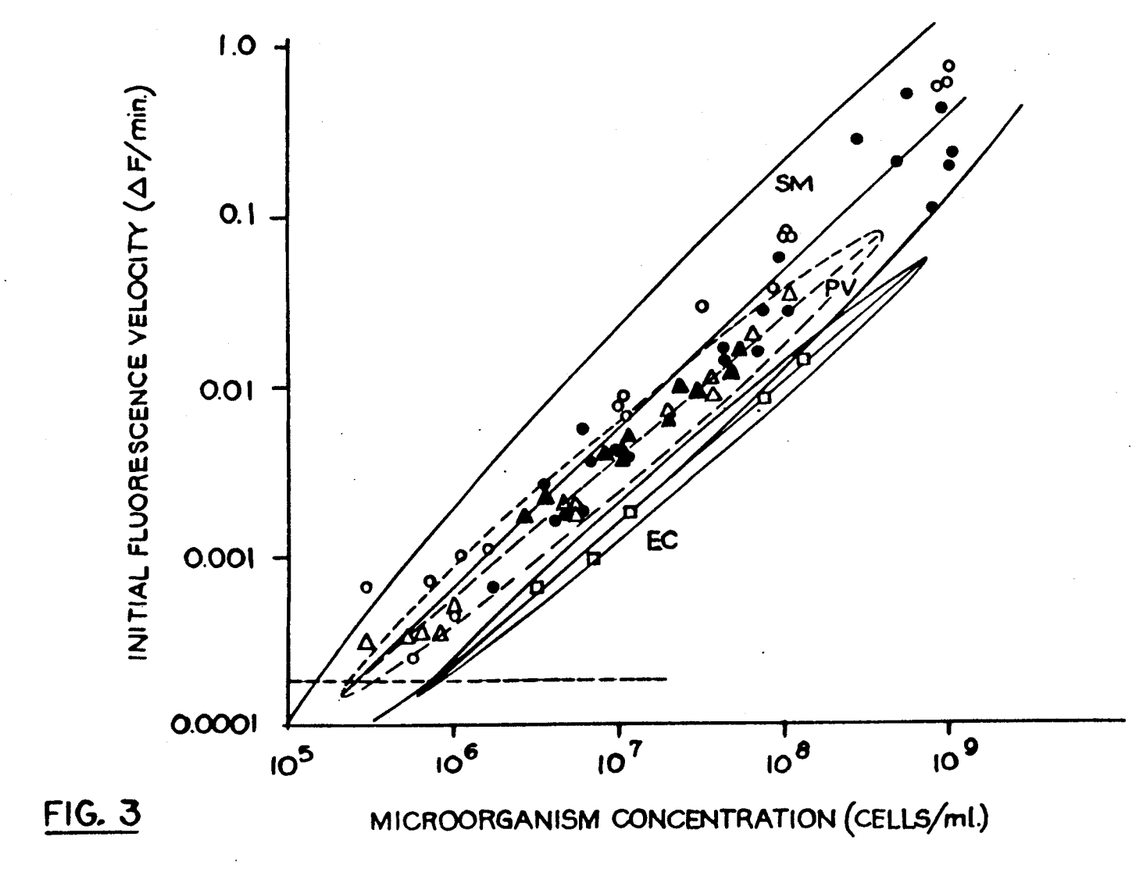
FIG. 3 illustrates a graph showing the initial velocity of indoxyl fluorescence from the substrate indoxyl acetate as a function of microorganism concentration. Each symbol represents a separate microbial suspension. The horizontal line at 0.00018 $\Delta F$/min. represents the substrate spontaneous hydrolysis fluorescence rate. This graph illustrates the microorganisms SM, PV and EC, wherein EC is represented by ($\square$), SM is represented by (O, ●) and PV is represented by ($\Delta$, $\blacktriangle$).
Figure 4:
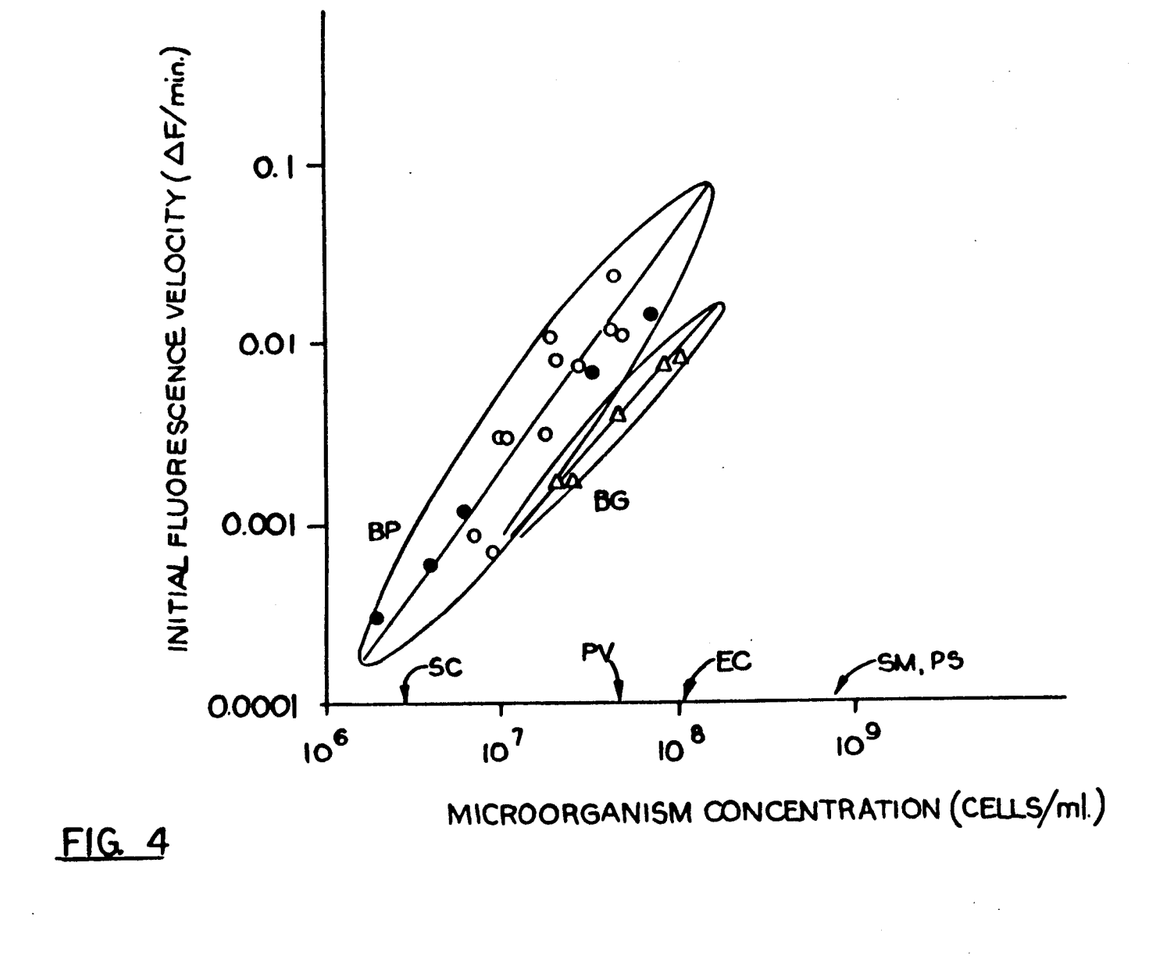
FIG. 4 is a graph of the initial velocity of indoxyl fluorescence from the substrate indoxyl glucoside as a function of bacteria concentration. No measureable substrate spontaneous hydrolysis was observed. Each symbol represents a separate microbial suspension. BG is illustrated by ($\Delta$), while BP is represented by (O, ●).

Indoxyl Acetate. FIGS. 2 and 3 represent the relative rate of fluorescence response with the organisms BG, BP, SC, PS, SM, PV and EC, and the non-fluorescent dye indoxyl acetate. The similarity in vertical displacement of the slopes reinforces the fact that the same type of enzyme (lipase/esterase, See Table 1) was monitored. At concentrations of less than $10^6$ cells per ml, no esterase reaction interference would be observed with the presence of PS, PV, SM and EC in the detection of the bacilli BG and BP. At similar concentrations of less than $10^4$ cell/ml, BG would be the only detectable organism in the presence of the other organisms. SC and BP display similar kinetics while the two organism groups SM, PV and EC, PS display virtually identical lipase activity within each group, the two groups being closely related in terms of lipase activity.

Indoxyl-$\beta$-D-Glucoside. With respect to FIG. 4, a fairly high detection limit of approximately $10^6$ cell/ml is noted for the bacilli activity. However, the remaining microorganisms are not detected.

Figure 5:
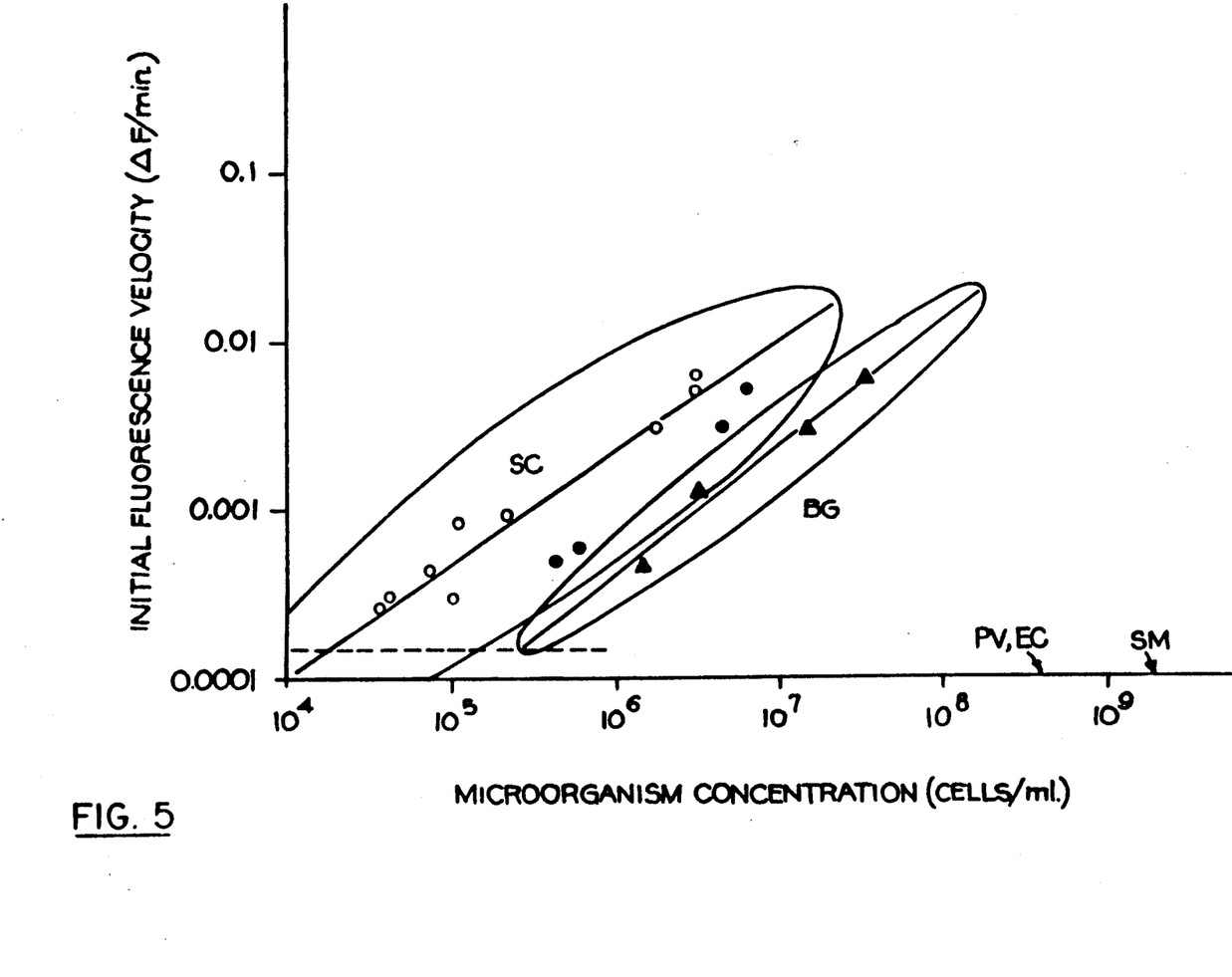
FIG. 5 is a graph of the initial velocity of 4-methylumbelliferone fluorescence from the substrate 4MU-glucoside as a function of microorganism concentration. The dashed line at 0.00015 $\Delta F$/min. represents the substrate spontaneous hydrolysis fluorescence rate. Each symbol represents a separate microbial suspension. The microorganism SC is represented by (O, ●), while the microorganism BG is represented by ($\blacktriangle$).
Figure 6:
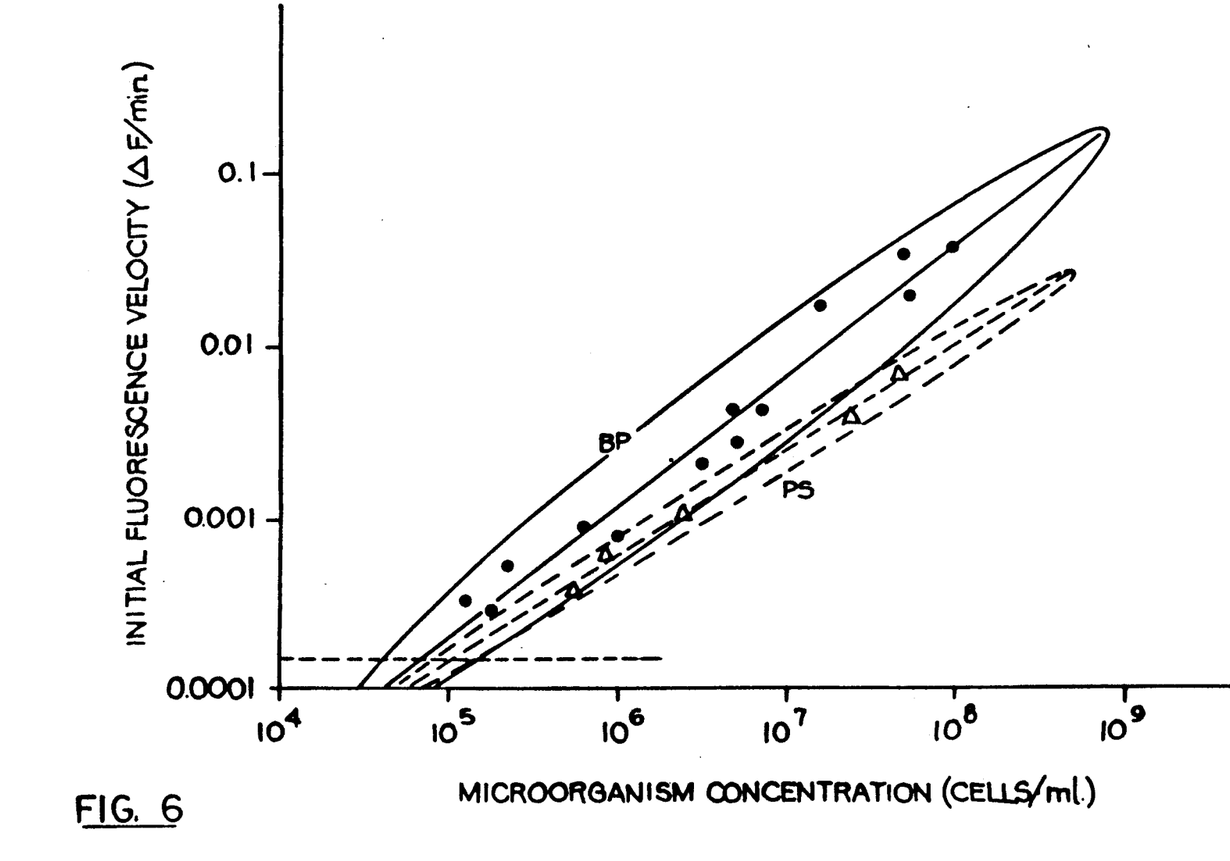
FIG. 6 is a graph of the initial velocity of 4-methylumbelliferone fluorescence from the substrate 4MU-glucoside as a function of microorganism concentration. The dashed line at 0.00015 $\Delta F$/min. represents the substrate spontaneous hydrolysis fluorescence rate. Each symbol represents a separate microbial suspension. The microorganism BP is represented by (●), while the microorganism PS is represented by ($\Delta$).

4MU-$\beta$-D-Glucoside. By probing the same $\beta$-D-Glucosidase enzyme with another glucoside non-fluorescent dye, the pattern of response is quite different with at least an order of magnitude of greater sensitivity. FIGS. 5 and 6 show that bacilli along with SC and PS organisms are able to generate fluorescence response. However, the two bacilli BG and BP, SC and PS display similar kinetics such that differentiation based upon these Figures alone would be difficult at best.

Figure 7:
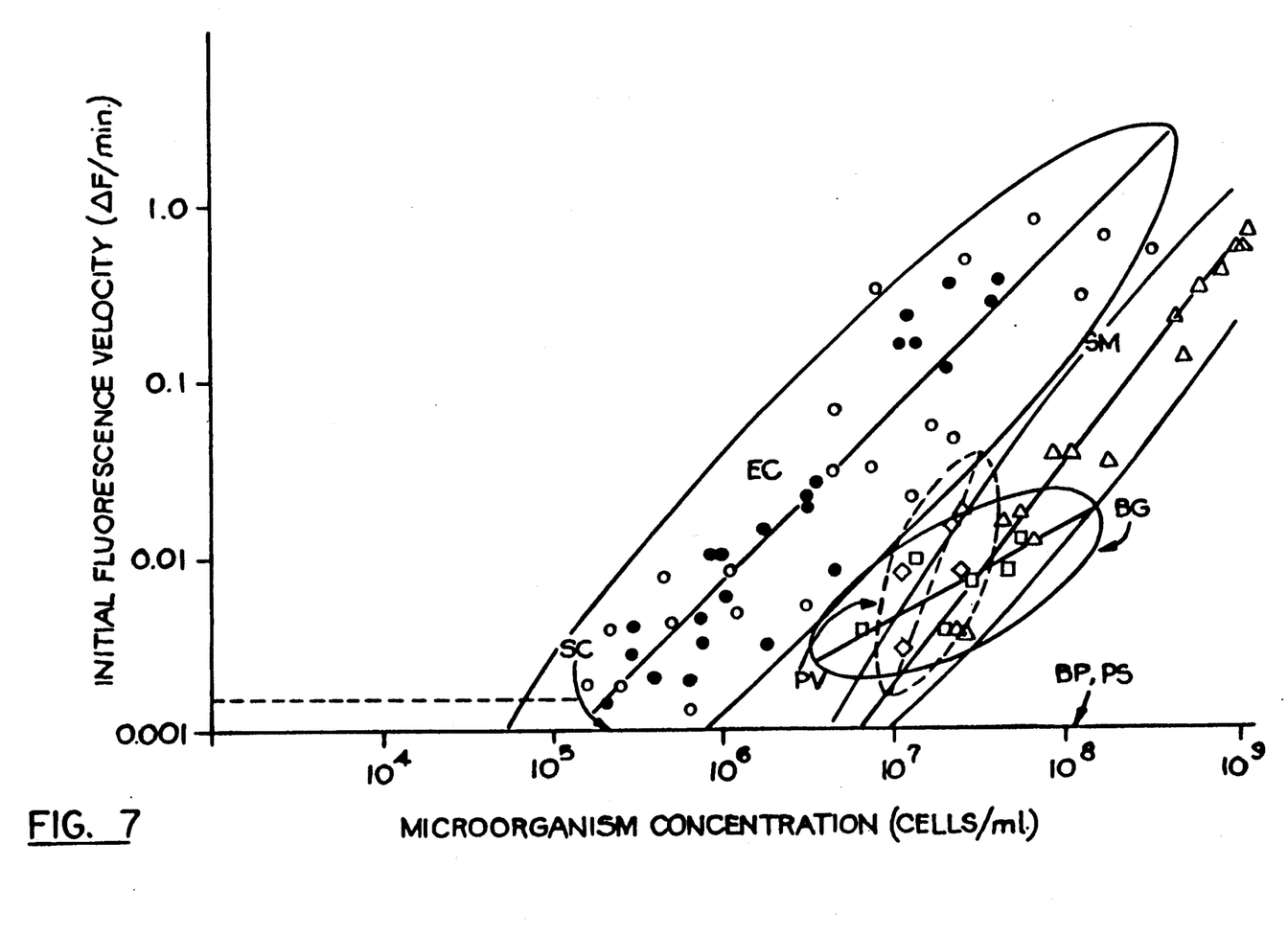
FIG. 7 is a graph of the initial velocity of 4-methylumbelliferone fluorescence from the substrate 4MU-phosphate as a function of microorganism concentration. The dashed line at 0.00015 $\Delta F$/min. represents the substrate spontaneous hydrolysis fluorescence rate. Each symbol represents a separate bacterial suspension. The microorganism EC is represented by (O, ●); the microorganism SM is represented by ($\Delta$); and the microorganism PV is represented by ($\Diamond$) and the microorganism BG is represented by ($\square$). The microorganisms SC, BP and PS had a very low fluorescence velocity and thus are only generally indicated in the graph.

4MU-Phosphate. FIG. 7 shows that by probing the phosphatase enzyme, a different grouping of organisms display a fluorescence response. EC appears to be the most sensitive and reactive to the phosphate substrates, while the presence of similar concentrations of the organisms SM and PV would cause no more than a 4% and 7%, respectively, fluorescence interference. However, BG, SM and PV display similar kinetics, each contributing no more than a 5% fluorescence interference, respectively, in the presence of similar concentrations of EC.

Figure 8:
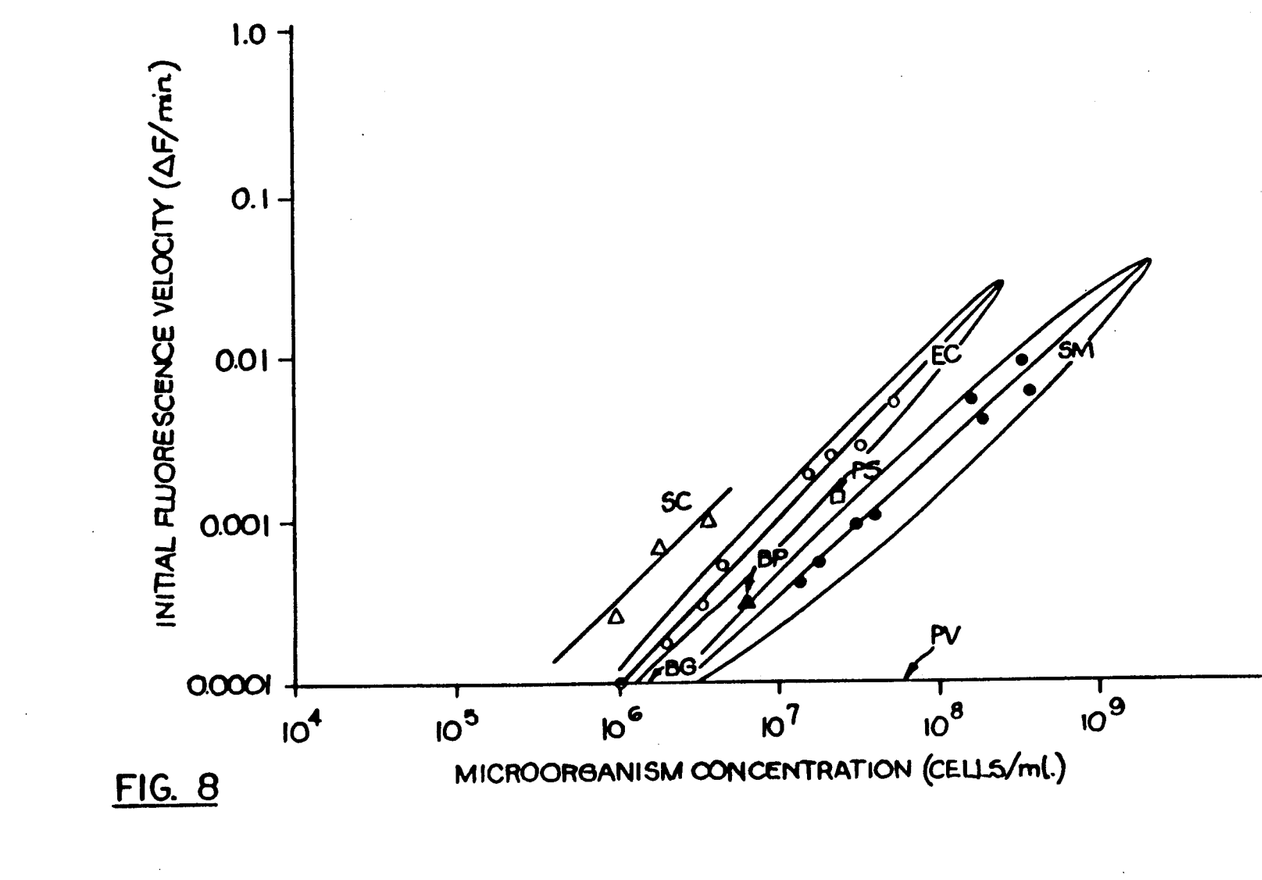
FIG. 8 is a graph of the initial velocity of indoxyl fluorescence from the substrate 3-indoxyl phosphate as a function of microorganism concentration. No measureable substrate spontaneous hydrolysis was observed. The microorganisms SC, BP, PS, EC and SM contain sufficient amount of data to be illustrated, wherein SC is illustrated by ($\Delta$); EC is represented by (O); SM is represented by the (●); PS is represented by the ($\square$); and BP is represented by the ($\blacktriangle$). The microorganisms BP and PV had such a low initial fluorescence velocity that they are merely represented in a general manner on the graph.

3-Indoxyl Phosphate. As opposed to the 4MU derivatives, SC can be detected with only a 10% interference effective in the presence of SM, at similar concentrations (FIG. 8). The presence of EC, PS and BP, however, would obscure the fluorescence response of SC, while BG and PV have no fluorescent response at the indicated bacterial concentrations.

Figure 9:
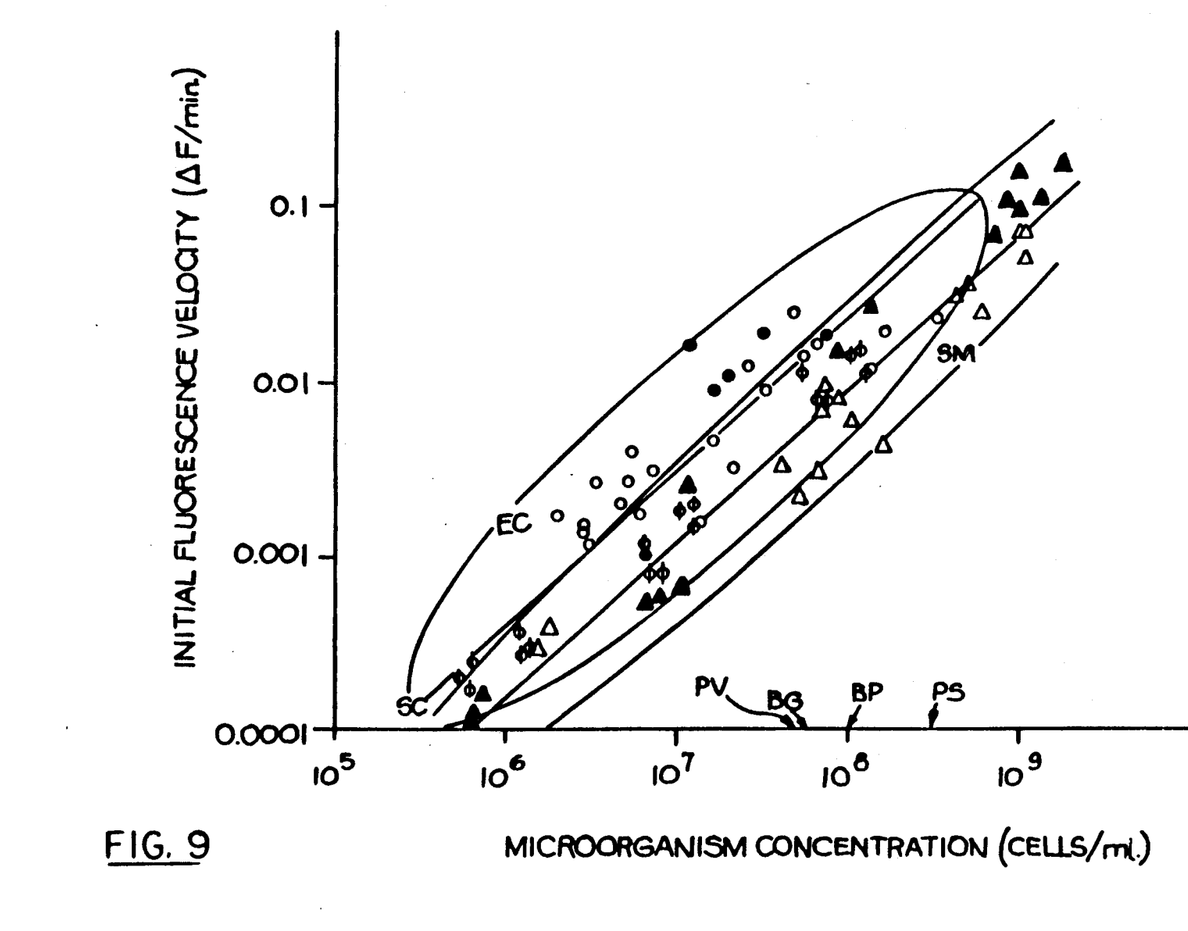
FIG. 9 is a graph of the initial velocity of 4-methylumbelliferone fluorescence from the substrate 4MU-galactoside as a function of microorganism concentration. No measureable substrate spontaneous hydrolysis was observed. Each symbol represents a separate bacterial suspension. The microorganism EC is represented by (O, ●, $\phi$), while the microorganism SM is represented by ($\Delta$, $\blacktriangle$). The microorganisms SC, PV, BG, BP and PS are generally indicated on the graph because their initial fluorescence velocity is too low to be accurately represented.

4MU-β-D-Galactoside. The response with this non-fluorescent dye is apparent in that only EC and SM produce fluorescence, while the other five organisms display no activity as illustrated in FIG. 9. The responses are, however, similar with SM producing approximately 40% of a fluorescence contribution as compared to that of EC at similar concentrations.

Table 3 depicts a qualitative pattern recognition tabulation of the quantitive pattern recognition set represented in FIGS. 1–9. A qualitative accounting of microbial responses as set forth in Table 3 can be used as the first step in the determination of microorganism identity and approximate concentration analysis. A sample of microorganisms is subjected to each non-fluorescent dye solution and the presence or absence of fluorescence is noted. Whether a single organism or a group of organisms are present, a pattern of fluorescent responses can be discerned. A comparison of the fluorescent responses as noted in Table 3 can lead to a reduction in the number of possible microorganisms present.

Because the production of fluorescence depends upon the presence of viable organisms, evaluation of the viability of the microorganisms as a function of the energy input is of concern. In particular, the excitation energy must be sufficient to probe the biochemistry without deactivating the microorganism itself. In the evaluation, laser energy was delivered at a high rate for a short time period or, alternatively, at a lower rate over a relatively longer period of time with total energy input remaining the same in each instance. It was discovered that at a given energy irradiation condition, approximately 70–75% of the microorganisms survived with apparently no discernible effect due to either the frequency or power input.

An order of magnitude light-scattering microorganism concentration determination of the sample would greatly facilitate the decision-making process. The measurement, however, produces a total microbial count without viable/non-viable discrimination. The measurement is valuable in that microorganism/non-fluorescent dye pairs can be eliminated which have detection limits higher than that of the light-scattering concentration determination, because they would have to be present at those higher concentrations in order to observe a fluorescent reaction with the respective reactant dye. However, in order to detect concentrations of particular microorganisms, it is desirable to have as concentrated a sample as possible. Table 2 indicates that a concentration detection limit less than or equal to $10^6$ cells/ml encompasses 50% of the organism/non-fluorescent dye pairs. Thus, it can be generalized from Table 2 that a contribution level less than $10^3$ cells/ml, for example, will be of insignificant value.

Microorganisms contain numerous enzymes with which to carry out their normal functions. The majority of enzymes are intracellular which precludes a rapid fluorescence, enzymatic kinetic analysis. Extracellular enzymes, on the other hand, can be probed in a rapid and convenient fashion. Some of these enzymes include lipase, β-glucosidase, phosphatase and β-glactosidase as set forth in Table 1.

The β-lactamases, penicillinase and cephalosporinase are other extracellular enzymes that may be included in the pattern recognition set because an in vivo reaction with the non-fluorescent penicillin (ampicillin and amoxicillin) and cephalosporin (cephalosporin C, cephaloglycin, cephalexin and cefadroxil) produce fluorescent products that are derivatives of either penicilloic acid or cephalosporic acid, respectively.

Thiaminase I and II are two other extracellular enzymes found in microorganisms such as Candida, Bacillus, and Clostridium. With the aid of an organic base or thiol compound, the enzymes catalyze the cleavage of the substrate thiamin (Vitamin B-1) to the fluorescent tricyclic product 2-Methyl-8-Ribosylcytosichrome.

Although the present invention sets forth certain microorganisms, a pattern recognition set can be developed for the majority of microorganisms. For example, pathogenic microorganisms such as Streptococcus, Salmonella, Staphylococcus, Streptomyces and Candida could be reacted with a particular non-fluorescent dye to produce a fluorescent product and thus a pattern recognition set for these pathogenic microorganisms.

Modification of the present invention may be made without departing from the spirit of it.

TABLE 1

| Enzyme Substrates | | |
|---|---|---|
| Substrate | Enzyme Probed | Response[b] |
| indoxyl acetate | lipase/esterase | + |
| N-methylindoxyl acetate | " | + |
| N-methylindoxyl myristate | " | + |
| β-naphthyl acetate | " | + |
| 5-bromoindoxyl acetate | " | + |
| 5-Br-4-Cl-3-indolyl acetate | " | + |
| diacetylfluorescein | lipase/esterase | + |
| 4MU-β-D-galactoside[a] | β-D-galactosidase | + |
| 4MU-phosphate | " | + |
| 3-indoxyl phosphate | " | + |
| indoxyl-β-D-glucoside | β-D-glucosidase | + |
| 4MU-β-D-glucoside | " | + |
| 6-Br-2-naphthyl-β-D-glucoside | " | +[c] |

[a] 4methylumbelliferyl
[b] A (+) indicates fluorescense was observed with some or all of the organisms.
[c] A response of 0.004 F/min with $2.0 \times 10^7$ cells/ml of BP was obtained monitoring 6-Br-β-naphthol fluorescence. This is similar in response with the substrate indoxyl glucoside.

TABLE 2

Limits of Microorganism Detection with Different Substrates in Phosphate/Tris Buffer Systems

| Substrate | $\Delta F/min$ detection limit[a] | Organism | | | | | | |
|---|---|---|---|---|---|---|---|---|
| | | BG | BP | SC | PS | PV | SM | EC |
| diacetylfluorescein | 0.022 | $3.8 \times 10^{3b}$ | $1.2 \times 10^5$ | $4.5 \times 10^4$ | $2.3 \times 10^6$ | $8.7 \times 10^6$ | $1.6 \times 10^7$ | $3.5 \times 10^8$ |
| indoxyl acetate | 0.00036 | $3.6 \times 10^2$ | $1.1 \times 10^4$ | $2.5 \times 10^4$ | $2.6 \times 10^6$ | $5.5 \times 10^5$ | $6.0 \times 10^5$ | $1.8 \times 10^6$ |
| indoxyl glucoside | $0.00015^c$ | $2.5 \times 10^6$ | $1.5 \times 10^6$ | — | — | — | — | — |
| 4MU-glucoside | 0.0003 | $6.5 \times 10^5$ | $1.5 \times 10^5$ | $5.0 \times 10^4$ | $3.0 \times 10^5$ | — | — | — |
| 4MU-phosphate | 0.003 | $5.0 \times 10^6$ | — | — | — | $1.2 \times 10^7$ | $1.5 \times 10^7$ | $4.1 \times 10^5$ |
| indoxyl phosphate | $0.00015^c$ | — | $2.5 \times 10^{6d}$ | $4.5 \times 10^5$ | $2.5 \times 10^{6d}$ | — | $4.0 \times 10^6$ | $1.5 \times 10^6$ |
| 4MU-galactoside | $0.00015^c$ | — | — | — | — | — | $10^6$ | $3.5 \times 10^5$ |

[a]The detection limit represents twice the F/min value of the spontaneous hydrolysis of the substrate.
[b]viable cells/ml.
[c]No measurable spontaneous hydrolysis was observed at an instrumental sensitivity of 0.0001 F/min.

TABLE 3

Qualitative Microorganism Response with Different Substrates in Phosphate/Tris Buffer Systems

| Substrate/Organism | BG | BP | SC | PS | PV | SM | EC |
|---|---|---|---|---|---|---|---|
| diacetylfluorescein | + | + | + | + | + | + | + |
| indoxyl acetate | + | + | + | + | + | + | + |
| indoxyl glucoside | + | + | $3.0 \times 10^6$ | $10^9$ | $5.0 \times 10^7$ | $10^9$ | 1 |
| 4MU-glucoside | + | + | + | + | $4.0 \times 10^8$ | $2.0 \times 10^9$ | 4 |
| 4MU-phosphate | + | $1.2 \times 10^8$ | $2.0 \times 10^5$ | $1.2 \times 10^8$ | + | + | + |
| indoxyl phosphate | $1.5 \times 10^6$ | + | + | + | $6.0 \times 10^7$ | + | + |
| 4MU-galactoside | $5.5 \times 10^7$ | $10^8$ | $4.0 \times 10^5$ | $3.0 \times 10^8$ | $5.0 \times 10^7$ | + | + |

We claim:

1. A process for the detection, identification, and quantification of viable microorganisms of a minimum concentration not less than $10^3$ cells per ml within a time period of sixty minutes, comprising the steps of:

obtaining a plurality of samples suspected of containing viable microorganisms, preparing therefrom an array of separate samples each having different cellular concentrations by a magnitude of at least about 10;

adding the same non-fluorescent dye to a plurality of said array of separate samples, said dye being capable of being catalyzed by said suspected viable microorganisms;

reacting said dye with an enzyme produced by said viable microorganisms to yield a product which can be induced to fluoresce;

inducing fluorescence; and detecting the rate of product fluorescence of the reaction of each of said array of separate samples at different concentrations and identifying and quantifying the microorganisms based upon the particular dye employed and the rate of fluorescence of said produced product by comparison with a standardized series of curves constituting a pattern recognition set of fluorescent response rates.

2. The process of claim 1, wherein said non-fluorescent dye is diacetylfluoroescein, indoxyl acetate, indoxyl-$\beta$-D-glucoside, 4 methylumbelliferone-$\beta$-D-glucoside, 4 methylumbelliferone-phosphate, $\beta$-indoxyl phosphate, or methylumbelliferone-$\beta$-D-glucosidase.

3. The process of claim 1, wherein the microorganisms are *Bacillus globigii, Bacillus pumilis, Saccharomyces cerevisiae, Pseudomonas stutzeri, Proteus vulgaris, Serratia marcescens,* or *Escherichia coli.*

4. The process of claim 1, wherein said enzyme is selected from the group consisting of lipase, esterase, $\beta$-D-galactosidase, phosphatase, and $\beta$-glucosidase.

5. The process of claim 1, wherein said process is completed in less than one-half hour.

6. The process of claim 1, wherein said product which is induced to fluoresce is detected by a fluorimeter.

* * * * *